(12) United States Patent
Marka et al.

(10) Patent No.: US 9,016,916 B2
(45) Date of Patent: Apr. 28, 2015

(54) SURGICAL LAMP FIELD SHAPE

(75) Inventors: Rudolf Marka, Ismaning (DE); Rouven Rosenheimer, Munich (DE)

(73) Assignee: Trumpf Medizin Systeme GmbH + Co. KG, Saalfeld (DE)

( * ) Notice: Subject to any disclaimer, the term of this patent is extended or adjusted under 35 U.S.C. 154(b) by 644 days.

(21) Appl. No.: 12/487,167

(22) Filed: Jun. 18, 2009

(65) Prior Publication Data
US 2009/0318771 A1 Dec. 24, 2009

(30) Foreign Application Priority Data
Jun. 20, 2008 (EP) .................................... 08011294

(51) Int. Cl.
| | |
|---|---|
| A61B 1/06 | (2006.01) |
| F21S 4/00 | (2006.01) |
| A61B 19/00 | (2006.01) |
| F21V 23/00 | (2006.01) |
| F21V 23/04 | (2006.01) |
| H05B 33/08 | (2006.01) |
| F21W 131/202 | (2006.01) |
| F21W 131/205 | (2006.01) |
| F21Y 101/02 | (2006.01) |

(52) U.S. Cl.
CPC ............ A61B 19/5202 (2013.01); F21V 23/00 (2013.01); F21V 23/04 (2013.01); F21W 2131/202 (2013.01); F21W 2131/205 (2013.01); F21Y 2101/02 (2013.01); H05B 33/0803 (2013.01); H05B 33/0851 (2013.01)

(58) Field of Classification Search
CPC .................... A61B 19/5202; F21W 2131/205; F21W 2131/202; F21Y 2101/02; F21Y 2105/001; Y10S 362/804; Y10S 362/80

USPC .......... 600/249; 362/427, 277, 572, 573, 576, 362/220, 249.1, 249.11, 282, 287, 322, 419, 362/432, 800
See application file for complete search history.

(56) References Cited

U.S. PATENT DOCUMENTS

| | | | | |
|---|---|---|---|---|
| 3,005,087 A | * | 10/1961 | Klein .............................. | 362/33 |
| 3,191,023 A | * | 6/1965 | Jones et al. .................... | 362/220 |
| 3,437,803 A | * | 4/1969 | Schafer et al. .................... | 362/8 |
| 4,064,425 A | * | 12/1977 | Masson ........................... | 362/33 |

(Continued)

FOREIGN PATENT DOCUMENTS

| | | |
|---|---|---|
| EP | 1 433 998 | 6/2004 |
| EP | 1 568 934 | 8/2005 |

(Continued)

OTHER PUBLICATIONS

Byrd, Ethan et al., "LED Matrix Controller", University of Illinois, Dec. 9, 2003 <http://www.google.com/url?sa=t&rct=j&q=&esrc=s &frm=1&source=web&cd=10&ved=0CJUBEBYwCQ &url=http%3A%2F%2Fcourses.engr.illinois. edu%2Fece445%2Fprojects%2Ffall2003%2Fproject10_final_ paper.doc&ei=Ny8NU4y9M4b80gGy54H4CA &usg=AFQjCNEDtq0kgiR6fc-7QXVg0uUjOMNIIA>, 25 pages.*

(Continued)

*Primary Examiner* — Eduardo C Robert
*Assistant Examiner* — Jacqueline Johanas
(74) *Attorney, Agent, or Firm* — Fish & Richardson P.C.

(57) ABSTRACT

A surgical lamp includes a lamp body with illuminants emitting bundled light beams with axes intersect a central axis of the lamp body, and illuminants emitting bundled light beams with axes that do not intersect the central axis. The shape of the light field and the distribution of the light intensity can be modified by driving different illuminants.

27 Claims, 4 Drawing Sheets

(56) References Cited

U.S. PATENT DOCUMENTS

| | | | |
|---|---|---|---|
| 4,196,460 A * | 4/1980 | Schreckendgust | 362/231 |
| 4,280,167 A * | 7/1981 | Ellett | 362/33 |
| 4,608,622 A * | 8/1986 | Gonser | 362/573 |
| 4,884,008 A * | 11/1989 | Bossler et al. | 315/152 |
| 4,967,320 A * | 10/1990 | Paschal | 362/96 |
| 5,038,261 A * | 8/1991 | Kloos | 362/286 |
| 5,068,767 A * | 11/1991 | Koyama | 362/33 |
| 5,257,173 A * | 10/1993 | Ohmamyuda et al. | 362/235 |
| 5,473,524 A * | 12/1995 | Behringer | 362/294 |
| 5,497,295 A * | 3/1996 | Gehly | 362/581 |
| 5,539,626 A * | 7/1996 | Scholz | 362/237 |
| 5,752,776 A * | 5/1998 | Kunreuther | 400/82 |
| 5,803,905 A * | 9/1998 | Allred et al. | 600/249 |
| 6,120,164 A * | 9/2000 | Libin et al. | 362/269 |
| 6,402,351 B1 * | 6/2002 | Borders et al. | 362/395 |
| 6,513,962 B1 * | 2/2003 | Mayshack et al. | 362/583 |
| 6,633,328 B1 * | 10/2003 | Byrd et al. | 348/143 |
| 6,639,623 B2 * | 10/2003 | Howell et al. | 348/61 |
| 6,880,957 B2 * | 4/2005 | Walters | 362/276 |
| 7,311,410 B2 * | 12/2007 | Marka | 362/33 |
| 7,465,065 B2 * | 12/2008 | Marka | 362/232 |
| 7,562,999 B2 * | 7/2009 | Chen | 362/239 |
| 7,600,894 B1 * | 10/2009 | Simon | 362/244 |
| 7,911,351 B2 * | 3/2011 | Mackenzie et al. | 340/638 |
| 7,980,738 B2 * | 7/2011 | Chiang | 362/427 |
| 8,050,547 B2 * | 11/2011 | Fornasiero | 396/4 |
| 8,227,999 B2 * | 7/2012 | Van Herpen et al. | 315/250 |
| 8,454,197 B2 * | 6/2013 | Hauschulte et al. | 362/249.03 |
| 8,817,085 B2 * | 8/2014 | Hiltl et al. | 348/61 |
| 2004/0129860 A1 | 7/2004 | Thibaud et al. | |
| 2005/0057929 A1 * | 3/2005 | Yano et al. | 362/240 |
| 2005/0195599 A1 * | 9/2005 | Marka | 362/232 |
| 2005/0195601 A1 | 9/2005 | Marka | |
| 2005/0231945 A1 * | 10/2005 | Leibinger et al. | 362/231 |
| 2005/0259434 A1 * | 11/2005 | Pederson | 362/555 |
| 2005/0265024 A1 * | 12/2005 | Luk | 362/231 |
| 2006/0082997 A1 * | 4/2006 | Derrien et al. | 362/236 |
| 2006/0291204 A1 * | 12/2006 | Marka et al. | 362/239 |
| 2007/0014567 A1 * | 1/2007 | Rossner et al. | 396/429 |
| 2007/0030702 A1 * | 2/2007 | Held et al. | 362/647 |
| 2007/0041167 A1 * | 2/2007 | Nachi | 362/33 |
| 2008/0232086 A1 * | 9/2008 | Marka et al. | 362/85 |
| 2008/0247163 A1 * | 10/2008 | Chen | 362/237 |
| 2008/0273317 A1 * | 11/2008 | Kaletin et al. | 362/33 |
| 2009/0262067 A1 * | 10/2009 | Feng et al. | 345/102 |
| 2011/0037840 A1 * | 2/2011 | Hiltl et al. | 348/61 |
| 2014/0066722 A1 * | 3/2014 | Marka et al. | 600/249 |

FOREIGN PATENT DOCUMENTS

| | | | | |
|---|---|---|---|---|
| EP | 1 568 937 | | 8/2005 | |
| EP | 1 722 157 | | 11/2006 | |
| RU | WO/2007/086770 | * | 8/2007 | A61B 19/00 |
| WO | WO2007086770 | | 8/2007 | |

OTHER PUBLICATIONS

Search Report from European Patent Office for European Application No. EP 08 01 1294, mailed Jan. 16, 2009, 4 pages.

* cited by examiner

SURGICAL LAMP FIELD SHAPE

CROSS REFERENCE TO RELATED APPLICATION

This application claims priority under 35 U.S.C. §119(a) to European Patent Application No. 08 11 294.9, filed Jun. 20, 2008, the entire contents of which are hereby incorporated by reference.

TECHNICAL FIELD

This invention relates to a surgical lamp with a light field having an adjustable size and shape and an adjustable light intensity distribution.

BACKGROUND

Surgical lamps fall under the international standard IEC 60601-2-41. This standard determines the requirements of lighting techniques of surgical lamps. Besides the characteristics of the color temperature, the brightness, and limits of radiation, the distribution of brightness in the light field is a characteristic of such surgical lamps. The diminution of brightness when the distance to the center of the light field increases is addressed in the above-noted international standard. The diameter of the light field at which the brightness is 50% of the maximum brightness must be at least half of the diameter of the light field at which the brightness is 10% of the maximum brightness with the lamp body and the operating plane separated by a distance of one meter.

Single reflector lamps are examples of surgical lamps that can fulfill these requirements. In single reflector lamps, the light source is a halogen lamp or a gas discharge lamp, arranged in the focal point of a single reflector having a diameter of about 500 mm to 1000 mm. By displacing the light source along the central axis of the reflector more or less out of the optimal focal point or into the optimal focal point, the diameter of the light field, i.e., the illuminated diameter in the operating field, is enlarged or narrowed. In addition, the focus point is shifted, i.e., the distance between the location which is most brightly illuminated where the reflected light beams intersect and the lamp body of the surgical lamp is changed along the central axis of the lamp body. In these types of lamps, the shape of the light field is circular and not modifiable due to construction.

Multi-reflector light systems constitute another type of construction. In these systems, the surgical lamp usually includes a central spotlight or a central light module, which is rigidly fixed to the lamp body, and several spotlights or light modules, which are annularly arranged about the central spotlight or the central light module. The change of the direction of the light emission of the outer spotlights or light modules is performed by radially pivotable illuminants or reflectors, or the entire spotlights or light modules are radially pivotably adjustable. Thus, the shape of the light field is adjustable such that the light field is circular at an ideal focusing and the light field more closely corresponds to a shape of the arrangement of the outer spotlights when the central axes of the outer spotlights intersect in a point which is not in the operating plane and when the distance between the focus point and the operating plane increases. The distribution of the light intensity changes from a concentric light distribution to a light distribution in which the beams of the outer spotlights are projected in the light field when the distance between the focal point and the operating plane increases.

In surgical lamps of other construction, the light field diameter and the distance of the focal point are not adjustable. In such lamps, the light characteristics are optimally adjusted for one operating point. The shape of the light field is circular. When using multi-reflector lamps, there is the risk that the light field no longer seems homogenous but several light points are projected in the operating area when the distance between the focus point and the operating plane is larger as described with regard to multi-reflector light systems.

The distribution of the light intensity in the light field can be varied by switching on and switching off the illuminants which centrically emit their light to the center of the light field.

For example, EP-A-1 568 034 depicts a surgical lamp with illuminants that can separately be switched on or switched off for enhancing the illumination of the center of the light field. The disclosure EP 1 568 934 depicts a surgical lamp with illuminants in the center of the light field, which can be switched off for avoiding shadowing. EP-A-1 722 157 depicts a surgical lamp with concentric regions, having illuminants that independently can be switched on or be dimmed for avoiding shadowing and optimally illuminating different types of operating wounds (e.g., narrow, deep wounds or widespread wounds). All of these references depict circular light fields at the operating point, i.e., at the optimal distance between the lamp body and the operating plane.

The publication EP-A-1 433 998 discloses a surgical lamp having several light modules which have bundles of light beams, the axes of which are parallel and the light fields of the bundles of light beams partly overlap and result in a shape of the light field which essentially results from the shape of the lamp body. For avoiding shadowing, several light modules are automatically switched off or dimmed. The shape of the light field is unalterable.

SUMMARY

In one aspect of the invention, a surgical lamp includes a lamp body having a central axis. The lamp body includes at least first, second, and third illuminants. The first illuminant is configured to emit a first bundle of light beams, the second illuminant is configured to emit a second bundle of light beams, and the third illuminant is configured to emit a third bundle of light beams. Axes of the first and second bundles of light beams are directed to a common point on the central axis, and an axis of the third bundle of light beams is directed to a point offset from the central axis.

In some embodiments, the illuminants comprise light emitting diodes.

In certain embodiments, the surgical lamp further includes a device adapted to dim the illuminants and to turn the illuminants on and off.

In some embodiments, the device is adapted to independently dim each of the elements and to independently turn each of the illuminants on and off.

In certain embodiments, the device is a current regulator.

In some embodiments, the surgical lamp includes multiple groups of illuminants, and the illuminants within each group are operable to together produce a light field.

In certain embodiments, one of the groups includes the first and second illuminants, and another group includes the third illuminant.

In some embodiments, the illuminants of one of the groups are evenly distributed over the lamp body.

In certain embodiments, the surgical lamp further includes a control device adapted to operate the groups of illuminants in a manner such that illuminants of a group including the first and second illuminants are activated to produce a circular light field.

In some embodiments, the illuminants of the group including the first and second illuminants are operated to emit brighter bundles of light beams than illuminants of any other group.

In certain embodiments, the surgical lamp includes a distance sensor configured to measure a distance between the lamp body and an operating site.

In some embodiments, the distance sensor is adapted to transmit distance information to the control device, and the control device is adapted to operate the illuminants based on the distance information received from the distance sensor.

In certain embodiments, the surgical lamp includes a brightness sensor configured to measure the brightness at an operating site.

In some embodiments, the brightness sensor is adapted to transmit brightness information to the control device.

In certain embodiments, the surgical lamp further includes a control device adapted to operate the groups of illuminants in a manner such that illuminants of a group including the third illuminant are activated to produce a non-circular light field.

In some embodiments, the illuminants of the group including the third illuminant are operated to emit brighter bundles of light beams than illuminants of any other group.

In certain embodiments, the control device includes memory that stores data for producing multiple different light field shapes.

In some embodiments, the surgical lamp further comprises a setting element for selecting a light field shape, and the setting element is adapted to transmit information regarding a selected light field shape to the control device.

In certain embodiments, the control device is adapted to operate the illuminants based on the information regarding the selected light field shape received from the setting element.

In some embodiments, the multiple different light field shapes include substantially rectangular light shapes, substantially triangular light shapes, and substantially oval light shapes.

In certain embodiments, the surgical lamp further includes a setting element for selecting a light distribution, and the setting element is adapted to transmit information regarding a selected light distribution to the control device.

In some embodiments, the control device is adapted to operate the illuminants based on the information regarding the selected light distribution received from the setting element.

In certain embodiments, the illuminants are arranged in a plane perpendicular to the central axis.

In some embodiments, the illuminants are attached to inclined fixing faces.

In another aspect of the invention, a method includes operating illuminants of a surgical lamp to produce a non-circular light field at an operation site.

In some embodiments, the surgical lamp includes a lamp body having a central axis, and at least some of the operated illuminants emit bundles of light beams having axes that are offset from the central axis of the lamp body at the operation site.

The surgical lamps described herein can allow the shape of the light field and the distribution of light intensity in the light field to be adjusted. The surgical lamp can be configured so that the shape of the light field and the distribution of the light intensity in the light field can be adjusted by a specific arrangement and control of the illuminants. This can be done without any mechanical adjustment devices.

Other aspects, features, and advantages of the invention are in the description, drawings, and claims.

DETAILED DESCRIPTION

Figure 1:
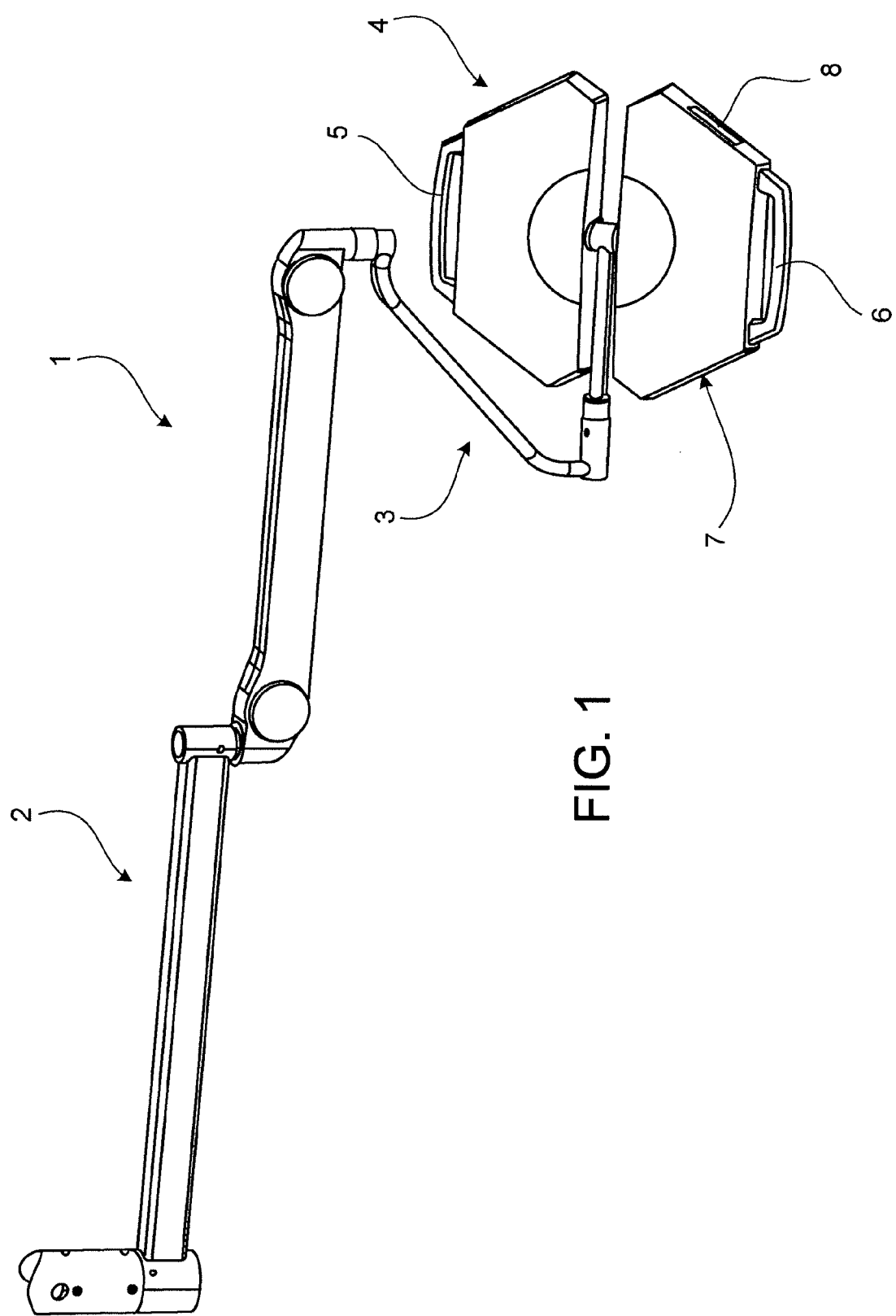
FIG. 1 is a perspective view of a surgical lamp.

FIG. 1 is a perspective view of a surgical lamp 1 that includes a carrying system 2, a suspension device 3, and a lamp body 4. The carrying system 2 can be fixed to a ceiling of a room, a wall, or a movable stand. Due to the carrying system 2 and the suspension device 3, the lamp body 4 is positionable at any of various different arbitrary positions and orientations within the range of action. A light emitting area is arranged on nearly the entire area of the opposite side of the lamp body 4, which is directed to an operation field during use.

For non-sterilly positioning of the lamp body 4, handles 5, 6 are attached to the two halves of the lamp body 4. The halves of the lamp body 4 are attached to one another in a torque-proof manner so that during pivoting of one of the halves, the other half accordingly moves to keep the light emitting areas in one plane.

In some embodiments, a control device 7 is arranged inside the lamp body 4. The control device 7 is not necessarily attached inside the lamp body 4. For example, in certain embodiments, the control device 7 is housed in a discrete housing that is attached to the lamp body 4 or the suspension device 3. Alternatively, the control device 7 can be located in an operating unit that is located in a medical supply unit or in/at a wall.

In some embodiments, an operating device 8 is arranged outside of the lamp body 4. The operating device 8 can alternatively be located in a separate housing that is, for example, located at the lamp body 4, at the suspension device 3, in a medical supply unit, or in/at a wall.

Figure 2:
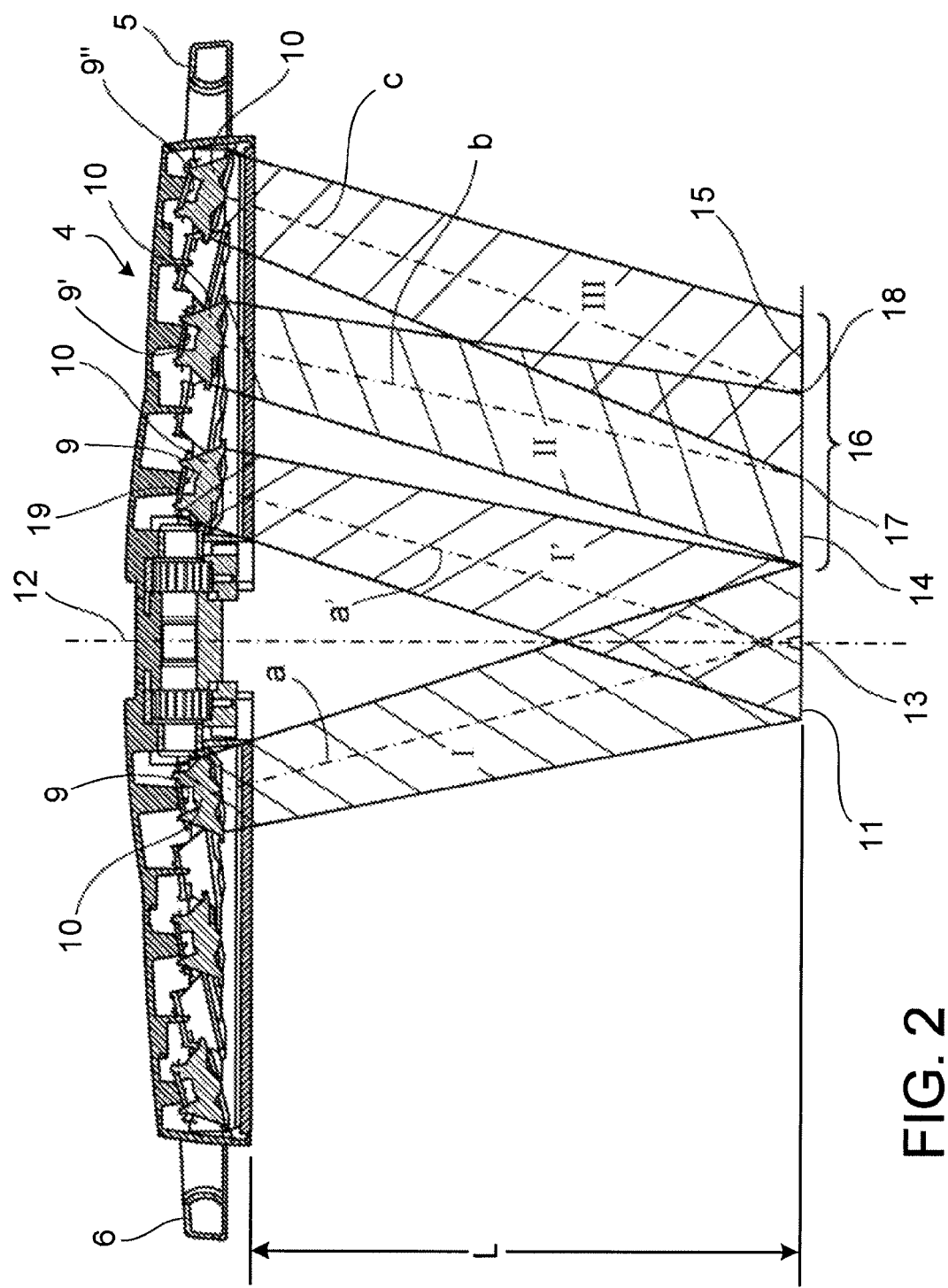
FIG. 2 is a sectional view of a lamp body of the surgical lamp emitting both light beams that do intersect a central axis of the lamp body and light beams that do not intersect the central axis of the lamp body.

FIG. 2 is a sectional view of the lamp body 4 that includes illuminants 9 emitting bundles of light beams I, I' with axes a, a' that intersect a central axis 12 of the lamp body 4. The lamp body 4 also includes illuminants 9', 9" emitting bundles of light beams II, III with axes b, c that do not intersect the central axis 12 of the lamp body 4.

The illuminants 9, 9', 9" are provided in the lamp body 4. The central axis 12 of the lamp body 4 is perpendicular to a plane in which the illuminants 9 are arranged. The illuminants 9, 9', 9" are circularly arranged or are arranged according to the shape of the lamp body 4.

Each of the illuminants 9, 9', 9" is provided with a device for bundling the light, here a refractor 10. As an alternative to refractors, reflectors can be used to bundle the light. In some embodiments, instead of using separate refractors or reflectors, an integrated device for bundling the light can be used.

The bundled light of the illuminants 9 emits in a bundle of light beams I, I' out of the refractors 10, which have axes a, a', respectively. The bundles of light beams I, I' illuminate an entire light field 11.

The illuminants 9 are secured to inclined fixing faces 19. Each of the inclined fixing faces 19 includes a perpendicular axis that is parallel to the axis a, a' of its associated light beam I, I'. The illuminants 9 with the refractors 10 are arranged so that the axes a, a' of the bundles of light beams I, I' intersect the central axis 12 at an intersection point 13.

In the description, an intersection point is to be understood to be not any geometrically exact point, but a region in which the axes intersect, whereby the lighting characteristics are within a common range of tolerance of an optimal intersection point. The range corresponds to an intersection area with a plane perpendicular to the central axis at a distance L.

Each of the bundles of light beams I, I' produces a light field in a plane perpendicular to the central axis 12 at a distance L from the lamp body 4. The intersection point 13, which is defined as a focus point, is the intersection point of each of the axes a, a' with the central axis 12 so that both of the light fields overlap and produce the light field 11. The light field 11 has a certain diameter D and a defined distribution of light intensity across the diameter of the light field, which is normatively determined. The overlapped light beams I, I' produce a light field which is approximately circular.

In FIG. 2, two illuminants 9 are shown as producing the central light field 11. The light field 11, however, is produced by a set of bundles of light beams I, I' that are emitted by the illuminants 9 that are evenly distributed over the light emitting area. The illuminants 9 with the refractors 10 are arranged so that the axes a, a' of the bundles of the light beams I, I' intersect the central axis at the intersection point 13.

The illuminants 9 are evenly distributed in the plane to shine beneath an object that is positioned between the lamp body 4 and the operation field. For example, if one bundle of light beams is blocked by the object, the light beams emitted by the other illuminants will be unaffected by the object and will thus continue to illuminate the light field. This helps to avoid or to reduce shadowing.

The bundled light of the illuminants 9' or 9" also emits from their associated refractor 10 in a bundle of light beams II or III, respectively, to produce a light field that is not centrally located.

The illuminants 9' 9" with the refractors 10 are arranged so that the axes b, c of the bundles of the light beams II, III do not intersect the central axis 12. In the view of FIG. 2, the axes b, c are projected in the plane of the drawing and the extrapolated axes would be depicted as to intersect the central axis in this plane. In a spatial depiction or in a projection in another plane, the axes b, c would not intersect the central axis (see FIG. 4).

The illuminants 9', 9" are fixed on associated inclined fixing faces 19 that have normal axes that are parallel to the axes b, c, respectively.

Each of the bundles of light beams II, III produces a light field 14, 15 in a plane perpendicular to the central axis 12 at a distance L from the lamp body 4. The illuminants 9', 9" with the refractors 10 are arranged so that the light fields 14, 15 partially overlap each other to obtain an even distribution of brightness.

In FIG. 2, only one illuminant 9', 9" is shown as producing each light field 14, 15, respectively. However, each of the light fields 14, 15 is produced by a sheaf or collection of bundles of light beams II, II that are emitted by additional illuminants 9', 9" that are not shown and that are evenly distributed in the plane to shine beneath an object that is positioned between the lamp body 4 and the operation field. For example, if one bundle of light beams is blocked by the object, the light beams emitted by the other illuminants will be unaffected by the object and will thus continue to illuminate the light field. This helps to avoid or to reduce shadowing. The light beams II, which form the light field 14, intersect at an intersection point 17, and the light beams II, which form the light field 15, intersect at an intersection point 18.

When using multiple illuminants 9, 9', 9", which are directed to the light fields 11, 14, 15 illuminants 9, 9', 9" having different colors can be used. Thereby, it is possible to adjust the resulting color temperature of the light in a certain range of color temperature.

In some embodiments, the illuminants 9 include LEDs. However, the illuminants 9 can alternatively include halogen lamps or gas discharge lamps. If necessary, the illuminants 9 can be provided with color filters.

The control device 7 is arranged in the lamp body 4. The control device 7 includes means for dimming and switching on and off of the illuminants 9, 9', 9", such as current regulators, means for transmitting switching commands and adjusting commands of the switching elements and adjusting elements of the operating device 8, a storage area for storing operation parameters, and a CPU which calculates and determines the necessary adjustments for the means for dimming and switching on and off the illuminants 9, 9', 9" from the switching and adjusting commands, based on stored operating parameters.

The control device 7 is connected to the illuminants 9, 9', 9", which are driven in groups. Each group is made up of several illuminants 9 or 9' or 9" that are driven with the same performance parameters. The several groups include: (1) illuminants 9 that are arranged to emit light beams I, I' having the identical intersection point 13; (2) illuminants 9' that are arranged to emit light beams II having the identical intersection point 17; and (3) illuminants 9" that are arranged to emit light beams III having the identical intersection point 18. Several groups of the illuminants 9 or the illuminants 9' or the illuminants 9" are possible, respectively.

The control device 7 is also connected to the operating device 8. The operating device 8 includes an element for switching the surgical lamp 1 on and off, an element for setting the shape of the light field, an element for setting the distribution of the brightness in the light field, an element for setting the distance between the lamp body 4 and the light fields I, I', II, III, and an element for setting the brightness of the light fields I, I', II, III.

The element for switching the surgical lamp 1 on and off switches the surgical lamp 1 from a standby-mode in which the illuminants 9 do not shine to an operating mode. Thereby, the illuminants 9 are driven according to the setting of the setting elements. For completely switching the surgical lamp 1 off by switching off the current supply, an external main switch is provided.

The element for setting the shape of the light field transmits the information concerning the selected shape of the light field of the surgical lamp 1 to the control device 7. When a circular light field is selected, the means for dimming and switching the surgical lamp 1 on and off are driven in such a way that only the illuminants that have an intersection point with the central axis 12 are activated.

When a light field different from a circular light field is selected, different parameters are stored in the control device 7. In some cases, the illuminants 9, 9', 9" can be operated to together form a substantially rectangular light field 16' by overlapping of their several light fields. Alternatively, oval light fields, dog bone shaped light fields, or triangular light fields can be formed. Optionally, it is possible to store parameters for producing arbitrary light fields in the storage area. Also, the dimensions, length and width, of the light fields are adjustable.

The element for setting the distribution of the light intensity transmits the setting information about the set distribution of the light intensity of the surgical lamp 1 to the control device 7. If a distribution of the light according to the standard is adjusted, the means for dimming and switching the surgical lamp 1 on and off are driven by the control device 7 such that only the illuminants 9 having intersection points located on the central axis 12 are activated.

To modify the distribution of the light intensity in the circular light field 11, additional illuminants 9 having light beams with axes that intersect points located on the central axis 12 but not at the intersection point 13 are activated. Consequently, by modifying the distribution of the light intensity, the diameter of the light field slightly increases (see FIG. 5).

Alternatively, illuminants can be applied having light bundle devices that do not constitute a light distribution according to the standard. For example, the distribution of the light intensity can be adjusted such that the periphery of the light field is illuminated more intensive and the center less intensive. By overlapping these light beams, the axes of the overlapped light beams are directed to the intersection point 13. Thus, with the light beams I, II, a desired distribution of the light intensity can be adjusted in accordance to the intensity of either of the different light beams (see FIG. 6).

The operating parameters for the distribution of the light intensity in a light field having a shape different from the circular shape can be empirically ascertained and stored.

The element for adjusting the distance between the light fields and the lamp body 4 transmits information to the control device 7 regarding the distance from the lamp body 4 to which the surgical lamp has to be adjusted.

In operation at a set distance L between the lamp body and the intersection point 13 on which the illuminants with the light beams I, I' are directed, the control device 7 of the present embodiment drives the illuminants 9 emitting the light beams I, I' with axes a, a' that are directed to the intersection point 13, and the approximately circular light field 11 is produced. When setting a different distance, alternative illuminants, the distance of the lamp body and the intersection point of the axes of their light beams of which corresponds to the set distance, are driven.

With settings when the set distance corresponds to one meter, the light field fulfills the normative requirements concerning the distribution of light intensity in the light field.

The element for setting the brightness transmits the adjustment information about the set general brightness of the surgical lamp 1 to the control device 7. The means for dimming and switching the surgical lamp 1 on and off are driven by the control device 7 such that the distribution of the brightness remains unchanged and the general brightness is merely changed.

The performance parameters for the brightness adjustments can be empirically ascertained and stored in the storage area of the control device 7.

In some embodiments, the surgical lamp 1 includes a distance sensor for measuring the distance between the lamp body 4 and the operation site and means for transmitting the distance to the control device 7. By detecting the distance between the lamp body 4 and the operating site and transmitting the distance information to the control device 7, the control device is capable of adjusting the point having the maximum resulting brightness at that distance from the lamp body 7 so that the operation site is illuminated with the greatest brightness.

In certain embodiments, the surgical lamp 1 includes a brightness sensor that detects the brightness in the operating site and means for transmitting the brightness information to the control device 7. By detecting the brightness, whereby one possibility is to detect the brightness in the center of the light field and another possibility is to detect the average brightness in the whole light field, and transmitting the brightness information to the control device 7, the control device 7 is capable of adjusting the point having the maximum resulting brightness at that distance from the lamp body 4 so that the operation site is illuminated with the identical brightness in the respective detection area when the distance of the lamp body 4 to the operating site is changed.

Figure 3:
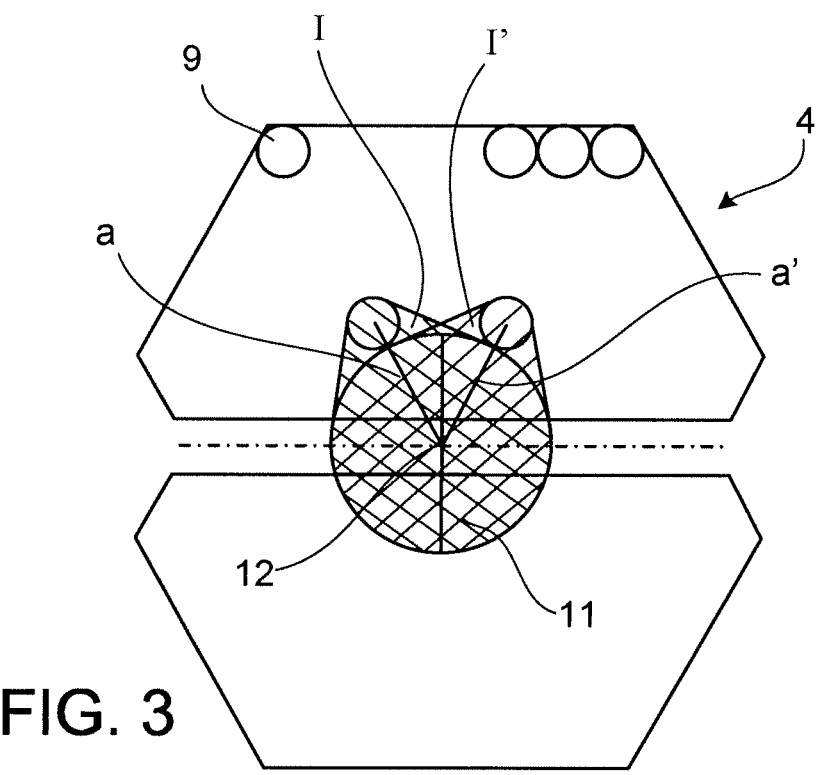
FIG. 3 is a diagrammatic plan view of a lamp body having an arrangement of illuminants that emit light beams with axes that intersect the central axis of the lamp body.

FIG. 3 shows a diagrammatic plane view of a lamp body 4 with an arrangement of illuminants 9 emitting the light beams I, I' with axes a, a' that intersect the central axis 12.

The entire light emitting area, meaning the lower side of both halves of the lamp body 4, is provided with illuminants 9 (here only five illuminants are shown). In this case, only those illuminants 9 arranged to emit the light beams I, I' with axes a, a' that intersect the central axis 12 are in operation. A circular light field is produced by these light beams I, I'.

Figure 4:
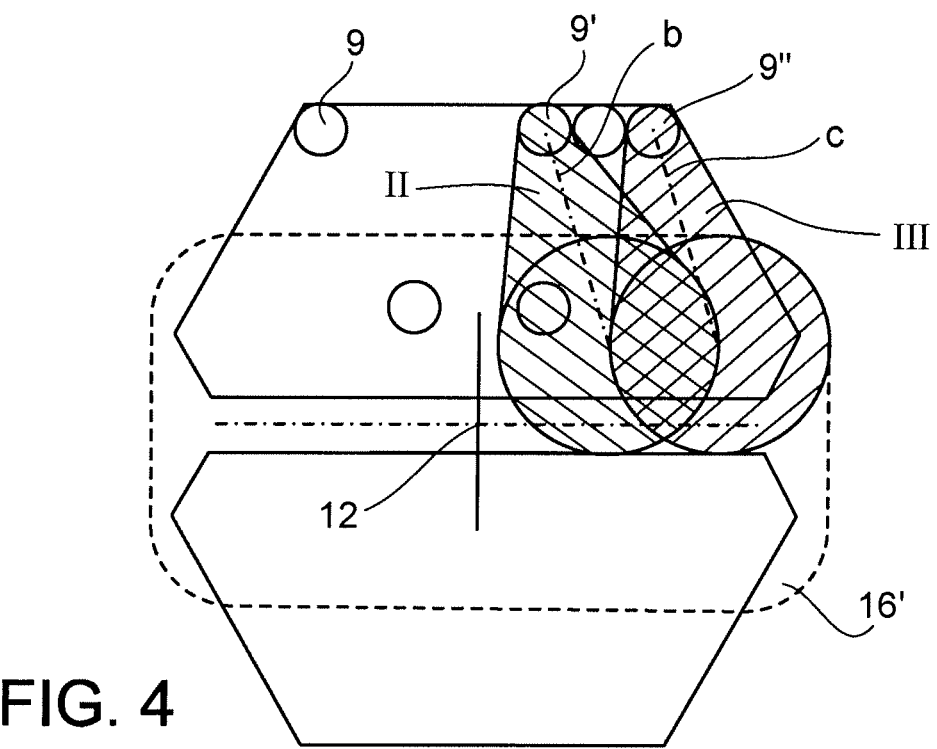
FIG. 4 is a diagrammatic plan view of a lamp body having an arrangement of illuminants that emit light beams that do not intersect the central axis of the lamp body.

FIG. 4 shows a diagrammatical plan view of a lamp body with an arrangement of illuminants 9. The axes a, a' of the light beams I, I' emitted by the illuminants 9 that are in operation do not intersect the central axis. In this case, the illuminants 9 that are in operation emit light beams II, III having axes b, c that do not intersect the central axis 12. By those light beams II, III, a part of an approximately rectangular light field is constituted. For constituting the central area of the light field, illuminants 9 that are arranged to emit light beams I, I' with axes a, a' that intersect the central axis 12 (see FIG. 3) can also be operated. The remaining area is illuminated by additional illuminants 9 arranged to emit light beams that do not intersect the central axis 12.

Figure 5:
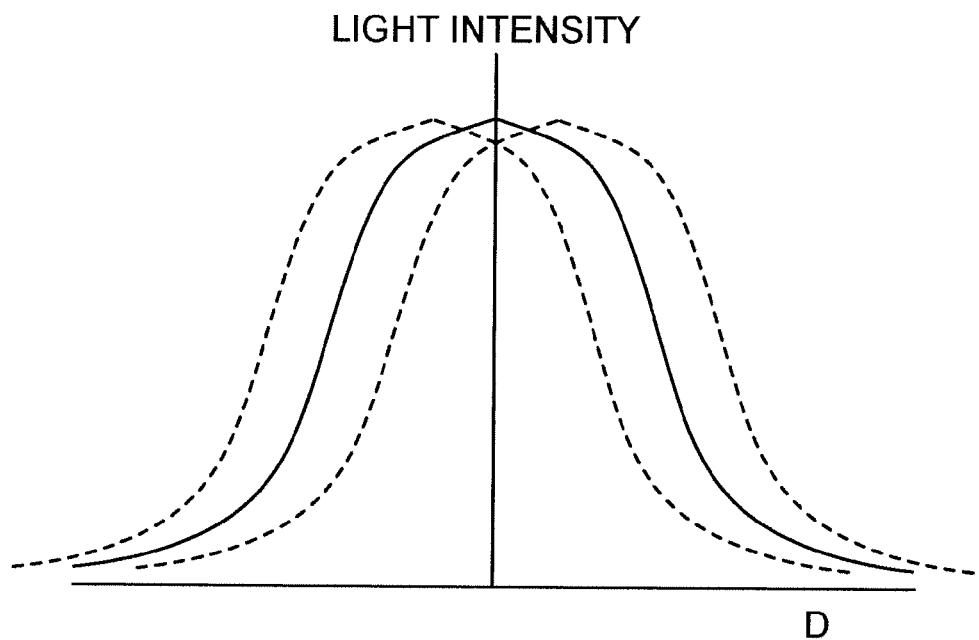
FIG. 5 is a graph of a distribution of light intensity across the diameter of the light field that results from devices for bundling light that create a normative light field.

FIG. 5 shows a distribution of the light intensity in a plane which is located a distance of one meter perpendicular to the central axis 12. Across the diameter of the light field, the light intensity of illuminants 9 with light bundle devices which constitute a standardized light field is shown here. The solid line depicts the distribution of the light intensity across a diameter D of the light field. This distribution is achieved when the axes of all of the light beams intersect at the intersection point 13. As a result of this, the normative requirements are fulfilled.

When operating additional illuminants, a principally normative light field, the intersection point of which is above or below the intersection point 13, can be produced. The light distribution across such a light field is depicted by dashed lines. In such a light field, the light beams overlap and the resulting light beam has a larger diameter with an enhanced brightness, whereby the maximum brightness in the center is reduced compared with the light beams I, I', which intersects at the intersection point 13.

The general brightness can be adjusted by proportional power adjustment of the respective illuminants.

Figure 6:
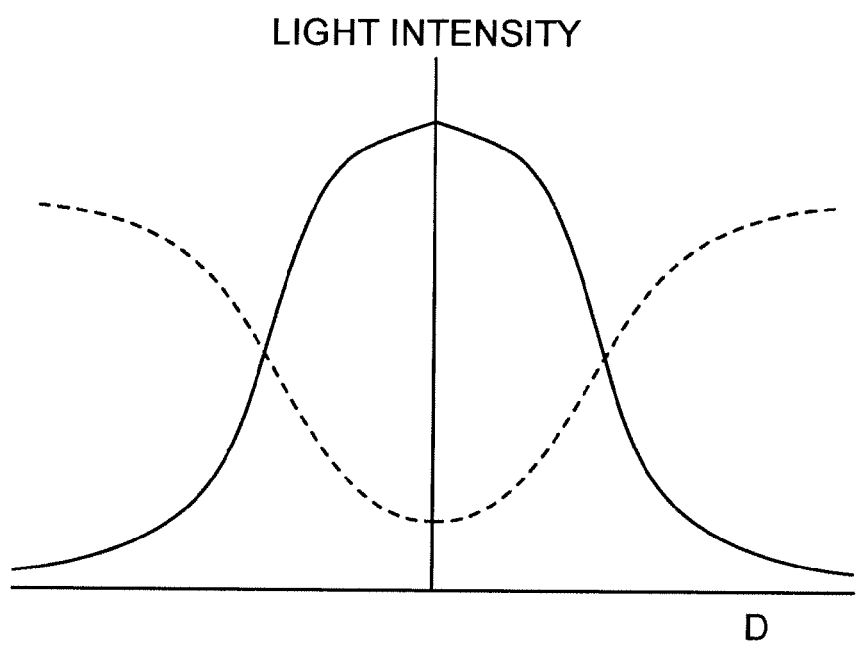
FIG. 6 is a graph of a distribution of light intensity across the diameter of the light field that results from devices for bundling light that create a normative light field, and that results from devices for bundling light that create a light field not conforming to the standard.

FIG. 6 shows the distribution of the light intensity across the diameter of the light field with light bundle devices that produce a normative light field and of the light bundle devices which do not produce a normative light field.

In this example, the distribution of the light intensity in a light field is shown by the dashed line, which is not normative. By superposing this light beam with a light beam that constitutes a normative distribution of light intensity (solid line, also see FIG. 5), a light field which nearly has a constant brightness across the entire diameter is produced.

Here, the general brightness is adjusted by proportional power adjustment of the respective illuminants.

The settings of the performance parameters for a normative light field distribution and for a light field distribution with constant brightness across the entire light field are stored in the storage area of the control device 7. However, it is possible to store an arbitrary light field distribution by the operator.

Other embodiments are within the scope of the following claims.

What is claimed is:

1. A surgical lamp, comprising:
   a lamp body having a central axis, the lamp body comprising first and second groups of illuminants, the first group comprising a first illuminant configured to emit a first bundle of light beams and a second illuminant configured to emit a second bundle of light beams, and the second group comprising a third illuminant configured to emit a third bundle of light beams,
   wherein axes of the first and second bundles of light beams are directed to a common point on the central axis, and an axis of the third bundle of light beams is directed to a point offset from the central axis;
   a control device adapted to operate the first and second groups of illuminants in a manner such that the surgical lamp can produce an overall light field having a shape that is non-circular; and
   a device adapted to independently adjust a brightness of the third illuminant and adapted to independently turn on and off the third illuminant according to data stored in the control device to adjust the third bundle of light beams directed to the point offset from the central axis such that the shape of the overall light field changes from a first shape of a plurality of defined light field shapes to a second shape of the plurality of defined light field shapes at an operation site,
   wherein the plurality of defined light field shapes is associated with the data and comprises substantially rectangular light field shapes or substantially oval light field shapes.

2. The surgical lamp of claim 1, wherein the illuminants comprise light emitting diodes.

3. The surgical lamp of claim 1, wherein the device is a current regulator.

4. The surgical lamp of claim 1, wherein the illuminants of the first group or the second group are evenly distributed over the lamp body.

5. The surgical lamp of claim 1, wherein the control device is adapted to operate the first and second groups in a manner such that the first group is activated to produce a circular light field.

6. The surgical lamp of claim 5, wherein the illuminants of the first group are operated to emit brighter bundles of light beams than the illuminants of any other group.

7. The surgical lamp of claim 5, wherein the surgical lamp further comprises a distance sensor configured to measure a distance between the lamp body and the operating site.

8. The surgical lamp of claim 7, wherein the distance sensor is adapted to transmit distance information to the control device, and the control device is adapted to operate the illuminants based on the distance information received from the distance sensor.

9. The surgical lamp of claim 5, wherein the surgical lamp further comprises a brightness sensor configured to measure the brightness at the operating site.

10. The surgical lamp of claim 9, wherein the brightness sensor is adapted to transmit brightness information to the control device.

11. The surgical lamp of claim 1, wherein the illuminants of the second group are operated to emit brighter bundles of light beams than the illuminants of any other group.

12. The surgical lamp of claim 1, wherein the control device comprises a memory that stores the data for producing the plurality of defined light field shapes.

13. The surgical lamp of claim 12, wherein the surgical lamp further comprises a setting element for selecting a light field shape of the plurality of defined light field shapes, and the setting element is adapted to transmit information regarding the selected light field shape to the control device.

14. The surgical lamp of claim 13, wherein the control device is adapted to operate the illuminants based on the information regarding the selected light field shape received from the setting element.

15. The surgical lamp of claim 12, wherein one or more of the plurality of defined light field shapes are generated from a combination of illuminants of the first and second groups of illuminants.

16. The surgical lamp of claim 1, wherein the surgical lamp further comprises a setting element for selecting a light distribution, and the setting element is adapted to transmit information regarding a selected light distribution to the control device.

17. The surgical lamp of claim 16, wherein the control device is adapted to operate the illuminants based on the information regarding the selected light distribution received from the setting element.

18. The surgical lamp of claim 1, wherein the illuminants are arranged in a plane perpendicular to the central axis.

19. The surgical lamp of claim 1, wherein the illuminants are attached to inclined fixing faces.

20. The surgical lamp of claim 1, wherein one of the first and second shapes is a circular shape, and the other of the first and second shapes is a non-circular shape.

21. The surgical lamp of claim 1, wherein the first and second shapes are non-circular shapes.

22. The surgical lamp of claim 1, wherein the control device is further adapted to independently adjust the brightness of the first and second illuminants and independently turn on and off the first and second illuminants to adjust the first and second bundles of light beams in cooperation with adjusting the third bundle of light beams.

23. A surgical lamp, comprising:
   a lamp body having a central axis, the lamp body comprising a group of first illuminants and a group of second illuminants, each of the first illuminants configured to emit a first bundle of light beams, and each of the second illuminants configured to emit a second bundle of light beams;
   a control device adapted to operate the groups of first and second illuminants in a manner such that an axis of each first bundle of light beams is directed to a common point on the central axis, and an axis of each second bundle of light beams is directed to a point offset from the central axis, such that the surgical lamp can produce an overall light field having a shape that is non-circular; and a device adapted to independently adjust a brightness of the second illuminants and adapted to independently turn the second illuminants on and off according to data stored in the control device to adjust the second bundle of light beams directed to the point offset from the central axis such that the shape of the overall light field changes from a first shape of a plurality of defined light field shapes to a second shape of the plurality of defined light field shapes at an operation site, wherein the plurality of defined light field shapes is associated with the data and comprises substantially rectangular light field shapes or substantially oval light field shapes.

24. The surgical lamp of claim 23, wherein one or more of the plurality of defined light field shapes are generated from a combination of illuminants of the first and second illuminants.

25. The surgical lamp of claim 23, wherein one of the first and second shapes is a circular shape, and the other of the first and second shapes is a non-circular shape.

26. The surgical lamp of claim 23, wherein the first and second shapes are non-circular shapes.

27. The surgical lamp of claim 23, wherein the control device is further adapted to independently adjust the brightness of the first illuminants and independently turn on and off the first illuminants to adjust the first bundle of light beams in cooperation with adjusting the second bundle of light beams.

* * * * *

UNITED STATES PATENT AND TRADEMARK OFFICE
CERTIFICATE OF CORRECTION

| | | |
|---|---|---|
| PATENT NO. | : 9,016,916 B2 | Page 1 of 1 |
| APPLICATION NO. | : 12/487167 | |
| DATED | : April 28, 2015 | |
| INVENTOR(S) | : Rudolf Marka et al. | |

It is certified that error appears in the above-identified patent and that said Letters Patent is hereby corrected as shown below:

In The Specification

On column 1, line 7, delete "08 11 294.9" and insert --08011294.9--.

Signed and Sealed this
Twenty-ninth Day of December, 2015

Michelle K. Lee
*Director of the United States Patent and Trademark Office*